United States Patent [19]
Mittendorf et al.

[11] Patent Number: 5,962,724
[45] Date of Patent: *Oct. 5, 1999

[54] HIGH ENANTIO-SELECTIVE PROCESS FOR PRODUCING PURE ENANTIOMERIC CYCLOPENTANE AND CYCLOPENTENE-(β)-AMINO ACIDS

[75] Inventors: Joachim Mittendorf; Hermann Arold; Peter Fey; Michael Matzke, all of Wuppertal; Hans-Christian Militzer, Bergisch Gladbach; Klaus-Helmut Mohrs, Wuppertal, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/666,492

[22] PCT Filed: Jan. 9, 1995

[86] PCT No.: PCT/EP95/00059

§ 371 Date: Jul. 5, 1996

§ 102(e) Date: Jul. 5, 1996

[87] PCT Pub. No.: WO95/19337

PCT Pub. Date: Jul. 20, 1995

[30] Foreign Application Priority Data

Jan. 13, 1994 [DE] Germany .............................. 44 00 749

[51] Int. Cl.⁶ .................................................. C07C 69/74
[52] U.S. Cl. .......................... 560/121; 435/135; 546/135; 556/418; 556/427; 556/438; 556/445; 558/432; 560/48; 560/76; 560/96; 560/64; 560/231; 562/503
[58] Field of Search ................................ 560/121, 96, 76, 560/64, 231, 48; 562/503; 558/432; 556/418, 438, 427, 445; 546/135; 435/135

[56] References Cited

U.S. PATENT DOCUMENTS 4,499,079 2/1985 Gordon ....................................... 514/2

FOREIGN PATENT DOCUMENTS 0571870 12/1993 European Pat. Off. .

OTHER PUBLICATIONS

P. Renold, et al., Tetrahedron: Asymmetry, vol. 4, No. 5, pp. 1047–1050, (1993).
H–J, Gais, et al., J. Org. Chem., vol. 54, pp. 5115–5122, (1989).
M. Schneider, et al., Angew. Chem. Int. Ed. Engl., vol. 23, No. 1, pp. 67–68, (1984).
Y. Morimoto, et al., Chem. Pharm. Bull., vol. 35, pp. 2266–2271, (1987).
J. Hiratake, et al., J. Chem. Soc. Perkin Trans. I, pp. 1053–1058, (1987).
J. Hiratake, et al., J. Chem. Soc., Chem. Commun., pp. 1717–1719, (1985).
R.A. Aitken, et al., Tetrahedron: Asymmetry, vol. 1, No. 8, pp. 517–520, (1990).
Chemical Abstracts, vol. 118, abstract No. 124085f, p. 762, (1993).
Derwent Abstracts, abstract of JP 63–287,754, Derwent Week 8902, (1988).

Primary Examiner—Michael L. Shippen
Attorney, Agent, or Firm—Sprung Kramer Schaefer & Briscoe

[57] ABSTRACT

The present invention relates to a highly enantioselective process for the preparation of enantiomerically pure cyclopentane- and -pentene β-amino acids of the general formula (I)

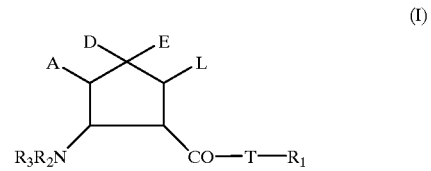

(I)

in which
A and L, A and D or E and L, D and E, R², R³, T and R¹ have the meaning given in the description.

5 Claims, No Drawings

HIGH ENANTIO-SELECTIVE PROCESS FOR PRODUCING PURE ENANTIOMERIC CYCLOPENTANE AND CYCLOPENTENE-(β)-AMINO ACIDS

The present invention relates to a highly enantioselective process for the preparation of enantiomerically pure cyclopentane- and -pentene β-amino acids.

The principle of an asymmetric ring opening of prochiral acid anhydrides with methanol and catalytic amounts of cinchona alkaloids is known from the publications J. Chem. Soc. Perkin Trans. I, 1987, 1053; Tetrahedron Asymm. 1990, 517 and J. Chem. Soc. Chem. Commun. 1985, 1717–1719. The corresponding half-esters are obtained with moderate enantiomeric excesses of from 35 to 67% of theory.

The invention relates to a highly enantioselective process for the preparation of enantiomerically pure cyclopentane- and -pentene β-amino acids of the general formula (I).

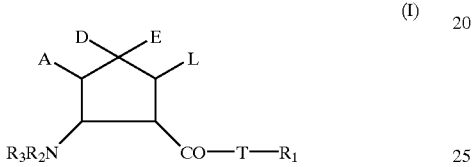

in which
A and L denote hydrogen
or
A and D or E and L in each case together form a double bond,
D and E are identical or different and represent hydrogen, halogen or hydroxyl or represent straight-chain or branched alkyl having up to 8 carbon atoms which is optionally mono- to disubstituted by identical or different substituents consisting of halogen, hydroxyl, phenyl, benzyloxy or carboxyl or of straight-chain or branched alkoxy, acyl or alkoxycarbonyl having in each case up to 6 carbon atoms or of a group of the formula —$NR^4R^5$,
in which
$R^4$ and $R^5$ are identical or different and denote hydrogen, phenyl or straight-chain or branched alkyl having up to 6 carbon atoms,
or D and E together represent a radical of the formula

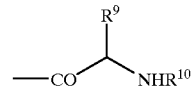

or =N—OH,
in which
$R^6$ and $R^7$ are identical or different and denote hydrogen or halogen or straight-chain or branched alkyl, alkoxy or oxyacyl having in each case up to 8 carbon atoms, or denote benzyl or phenyl,
or
D and E together represent the radical of the formula =O or =S,
$R^2$ represents hydrogen or
represents an amino-protecting group, or represents straight-chain or branched alkyl having up to 8 carbon atoms which is optionally mono- to disubstituted by identical or different substituents consisting of hydroxyl or formyl or of straight-chain or branched acyl having up to 6 carbon atoms or of phenyl or benzoyl, which are optionally substituted up to 2 times by identical or different substituents consisting of halogen, nitro or cyano or of straight-chain or branched alkyl having up to 6 carbon atoms,
or
represents straight-chain or branched acyl having up to 8 carbon atoms,
or
represents benzoyl which is optionally substituted as described above,
or
represents a group of the formula —$SO_2R^8$,
in which
$R^8$ denotes straight-chain or branched alkyl having up to 8 carbon atoms or denotes benzyl or phenyl, the latter radicals being optionally substituted up to 3 times by identical or different substituents consisting of halogen, hydroxyl, nitro, cyano, trifluoromethyl or trifluoromethoxy or of straight-chain or branched alkyl, alkoxy or alkoxycarbonyl having in each case up to 6 carbon atoms, or carboxyl or of the above-indicated group —$NR^4R^5$,
in which
$R^4$ and $R^5$ have the meaning given above,
or
represents phenyl which is optionally substituted up to 3 times by identical or different substituents consisting of halogen, hydroxyl, nitro, trifluoromethyl, trifluoromethoxy, straight-chain or branched alkyl, acyl, alkoxy or alkoxycarbonyl having in each case up to 6 carbon atoms or of a group of the formula —$NR^4R^5$ or —$SO_2R^8$,
in which
$R^4$, $R^5$ and $R^8$ have the meaning given above,
or
represent an amino acid residue of the formula

in which
$R^9$ denotes cycloalkyl having 3 to 8 carbon atoms, aryl having 6 to 10 carbon atoms or hydrogen or denotes straight-chain or branched alkyl having up to 8 carbon atoms,
the alkyl being optionally substituted by cyano, methylthio, hydroxyl, mercapto or guanidyl or by a group of the formula —$NR^{11}R^{12}$ or $R^{13}$—OC—,
in which
$R^{11}$ and $R^{12}$ independently of one another represent hydrogen, straight-chain or branched alkyl having up to 8 carbon atoms or phenyl,
and
$R^{13}$ denotes hydroxyl, benzyloxy or alkoxy having up to 6 carbon atoms or denotes the above-indicated group —$NR^{11}R^{12}$,
or the alkyl is optionally substituted by cycloalkyl having 3 to 8 carbon atoms or by aryl having 6 to 10 carbon atoms which is substituted in turn by hydroxyl, halogen, nitro or alkoxy having up to 8 carbon atoms or by the group —$NR^{11}R^{12}$,
in which
$R^{11}$ and $R^{12}$ have the meaning given above,
and
$R^{10}$ denotes hydrogen or an amino-protecting group, $R^3$ represents hydrogen or represents straight-chain or branched alkyl having up to 8 carbon atoms which is optionally substituted by phenyl, or $R^2$ and $R^3$ together represent the radical of the formula =$CHR^{14}$, in which $R^{14}$ denotes hydrogen or straight-chain or branched alkyl having up to 8 carbon atoms which is optionally substituted by halogen, hydroxyl, phenyl or carboxyl or by straight-chain or branched alkoxy or alkoxycarbonyl having in each case up to 6 carbon atoms, T represents an oxygen or sulphur atom or represents the —NH group, $R^1$ represents hydrogen or represents straight-chain or branched alkyl having up to 8 carbon atoms or phenyl, the latter radicals being optionally substituted up to 3 times by identical or different substituents consisting of hydroxyl, halogen, nitro, cyano, carboxyl, trifluoromethyl or trifluoromethoxy, of straight-chain or branched alkoxy, and in the case of phenyl also of straight-chain or branched alkyl, acyl or alkoxycarbonyl having in each case up to 6 carbon atoms, or of a group of the formula —$NR^4R^5$ or —$SO_2R^8$, in which $R^4$, $R^5$ and $R^8$ have the meaning given above, or, if T represents the —NH group, $R^1$ represents the group of the formula —$SO_2R^8$, in which $R^8$ has the meaning given above, characterized in that meso-dicarboxylic acid anhydrides of the general formula (II)

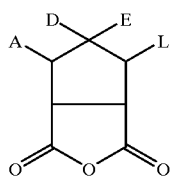

(II)

in which

A, D, E and L have the meaning given above are converted by an asymmetric alcoholysis with alcohols of the general formula (III)

$R^{15}$—OH (III)

in which $R^{15}$ represents straight-chain or branched alkyl or represents alkenyl having in each case up to 5 carbon atoms, which are optionally substituted by cyano, trimethylsilyl, phenyl or trichloromethyl, and in the presence of equimolar amounts of a chiral amine base which is present in enantiomerically pure form, in inert solvents and initially via the intermediate, enantiomerically pure salt stage of the general formula (IV)

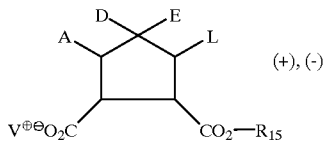

(IV)

in which

A, D, E, L and $R^{15}$ have the meaning given above and

V represents the chiral amine base, to the enantiomerically pure compounds of the general formula (IVa)

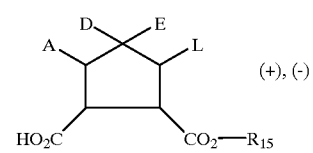

(IVa)

in which

A, D, E, L and $R^{15}$ have the meaning given above, subsequently, following activation of the free carboxylic acid function by reaction with liquid $NH_3$, the enantiomerically pure amides of the general formula (V)

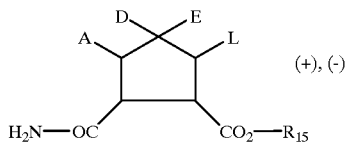

(V)

in which

A, D, E, L and $R^{15}$ have the meaning given above, are prepared, in a further step the products are converted, by elimination of the radical $R^{15}$ in inert solvents, enzymatically or in the presence of a Pd catalyst, and in each case depending on a nucleophilic auxiliary, into the compounds of the general formula (VI) or (VIa)

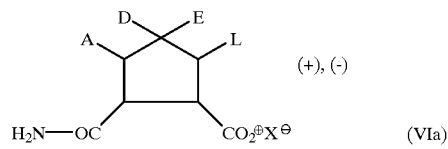

(VI)

(VIa)

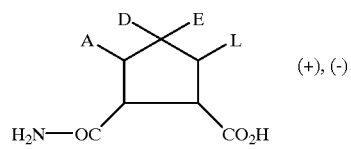

in which

A, D, E and L have the meaning given above, and

X represents an alkali metal or alkaline earth metal atom, preferably sodium, and finally a Hofmami rearrangement is carried out using alkali metal hypochlorites or alkaline earth metal hypochlorites in aqueous alkali metal hydroxide or alkaline earth metal hydroxide solution, the free amine function is initially blocked in solution with a typical amino-protecting group, which is eliminated by conventional methods after isolation of the protected compounds in accordance with conventional conditions, to obtain the respective pure enantiomer.

The process according to the invention can be illustrated by way of example by means of the following equation:

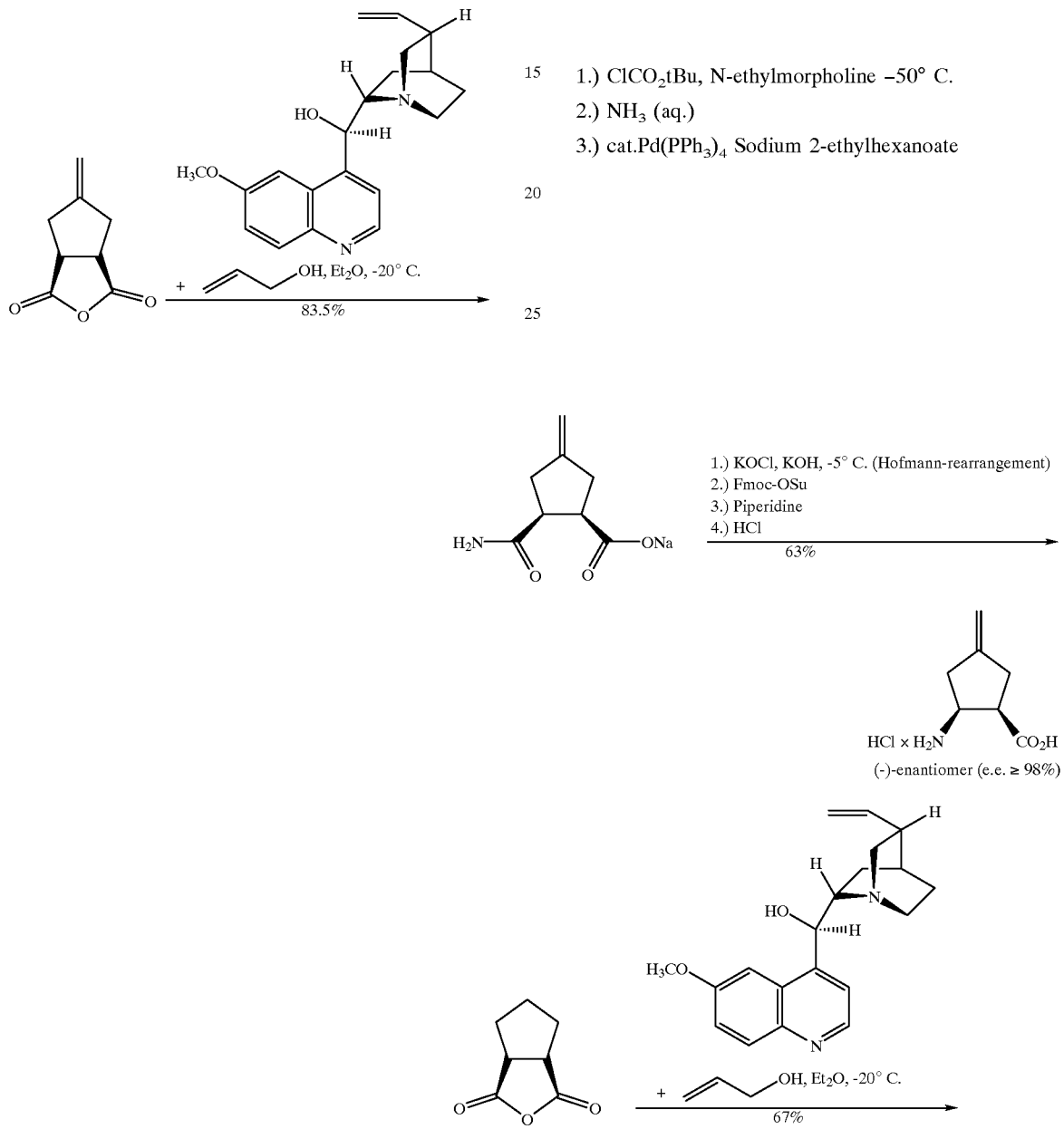

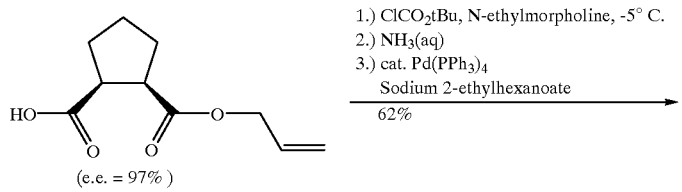

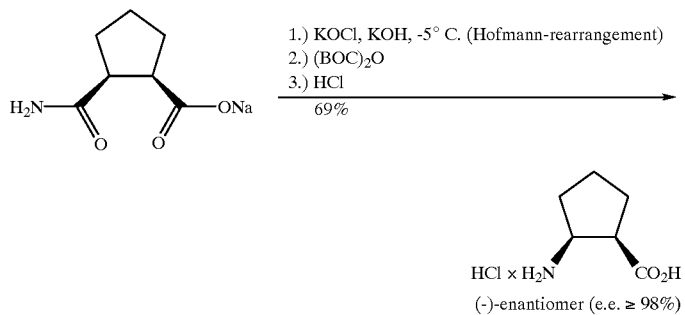

Surprisingly, when carrying out the process according to the invention, the chiral compounds of the general formula (I) are obtained in an elegant manner with a very high enantiomeric purity combined with very good yields.

In contrast to the above-cited prior art, the process according to the invention makes possible a highly enantioselective route to the opening of prochiral anhydrides in the presence of equimolar quantities of a chiral amine base, an additionally enantiomeric enrichment being brought about by crystallization of the intermediate salts of the corresponding dicarboxylic acid monoesters (formula IVa) with the chiral amine base. Even the dicarboxylic acid monoesters (formula IVa) are obtained in a good yield and in highly pure form. Furthermore, the process according to the invention is distinguished, in contrast to the prior art, by the fact that not only can the chiral amine base be recovered completely simply by extraction with dilute acids but also the dicarboxylic acid monoester (formula IVa), which is contained in the mother liquor at a somewhat lower enantiomeric purity, can be converted back in an elegant manner into the corresponding anhydride.

A further advantage of the process according to the invention, especially in view of the cost factor as well, is that the overall reaction sequence is very short and of low complexity, and that even the various intermediates are obtained and/or can be recovered in very good yields and with high enantiomeric purity.

Suitable solvents for the reaction of the dicarboxylic acid anhydrides of the general formula (II) are all inert organic solvents which are not changed under the reaction conditions. These include preferably ethers such as diethyl ether., dioxane, diisopropyl ether, tert-butyl methyl ether, tetrahydrofuran or glycol dimethyl ether, or hydrocarbons such as toluene, benzene, xylene, hexane, cyclohexane or petroleum fractions, or chlorinated hydrocarbons such as chloroform or methylene chloride, or amides such as dimethylformamide, dimethylacetamide or hexamethylphosphoric triamide, or glacial acetic acid, dimethyl sulphoxide, acetonitrile or pyridine. Diisopropyl ether, diethyl ether, dioxane, tert-butyl methyl ether and toluene are preferred for the individual steps.

The reaction temperatures can be varied over a relatively wide range. The reactions are in general carried out between −60° C. and +20° C., preferably between −20° C. and +25° C.

The reactions can be carried out at atmospheric pressure but also at elevated or reduced pressure (e.g. from 0.5 to 80 bar). They are generally carried out at atmospheric pressure.

Suitable alcohols (formula III) for the process according to the invention are preferably primary alcohols such as, for example, propanol, butanol, isopropanol, ethanol, allyl alcohol or cinnamyl alcohol.

Suitable chiral amine bases for the process according to the invention are preferably alkaloids and cinchona alkaloids. Particular preference is given to cinchona alkaloids such as, for example, (+),(−)-quinine, (+),(−)-hydroquinine, (+),(−)-cinchonidine, (+),(−)-epiquinidine, (+),(−)-epicinchonidine, (+),(−)-cinchonine, (+),(−)-epicinchonine, (+),(−)-epiquinine, (+),(−)-hydroquinidine, (+),(−)-4-chlorobenzoate-epiquinine or (+),(−)-4-chlorobenzoate-epicinchonine. (+),(−)-Quinine and (+),(−)-quinidine are particularly preferred.

The chiral amine base is employed in equivalent quantities based on 1 mol of the dicarboxylic acid anhydrides of the general formula (II).

Examples of suitable acids for the recovery of the free chiral amine base are mineral acids such as HCl, HBr or sulphuric acid.

The acid is generally employed in a quantity of from 1 mol to 10 mol, preferably from 1.5 mol to 4 mol, based on 1 mol of the compounds of the general formula (IV).

The recovery is generally carried out in a temperature range from 0° C. to +50° C., preferably from 20° C. to 30° C. at atmospheric pressure.

The amidation is generally carried out in inert solvents in the presence of a base and an activating reagent.

Suitable solvents in this context are inert organic solvents which are not changed under the reaction conditions indicated. These include esters such as methyl, ethyl, isopropyl or n-butyl acetate or ethers such as diethyl ether, dioxane, diisopropyl ether, tert-butyl methyl ether, tetrahydrofuran or glycol dimethyl ether, halogenated hydrocarbons such as dichloromethane, trichloromethane, tetrachloromethane, 1,2-dichloroethane, trichloroethane, tetrachloroethane or trichloroethylene, hydrocarbons such as benzene, xylene, toluene, hexane, cyclohexane or petroleum fractions, nitromethane, dimethylformamide, acetonitrile or hexamethylphosphoric triamide. It is also possible to employ mixtures of the solvents. Methyl acetate is particularly preferred.

Suitable bases for the amidation are organic amines such as N-ethylmorpholine, N-methylmorpholine, pyridine, triethylamine or N-methylpiperidine.

The amidation is generally carried out in a temperature range from −30° C. to +20° C., preferably at from −20° C. to 0° C.

The amidation is generally carried out at atmospheric pressure. However, it is also possible to carry out the process at subatmospheric pressure or at superatmospheric pressure (e.g. in a range from 0.5 to 5 bar).

Suitable activating reagents are carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphonate or propanephosphoric anhydride, or alkyl chloroformates such as ethyl or isobutyl chloroformate, or benzotriazolyloxy-tris-(dimethylamino)phosphonium hexafluorophosphate, or N,N-diphenylphosphonamide, or methanesulphonyl chloride, is optionally in the presence of bases such as triethylamine or N-ethylmorpholine or N-methylpiperidine.

The base is generally employed in a quantity of from 1 mol to 3 mol, preferably from 1 mol to 1.5 mol, based on 1 mol of the compounds of the general formula (IVa).

The radical $R^{15}$ is generally eliminated in inert solvents such as, for example, in the above-listed hydrocarbons, esters or ethers, in particular in tetrahydrofuran, acetonitrile, dimethylformamide or ethyl acetate. Ethyl acetate is preferred.

Examples of suitable nucleophilic auxiliaries for the elimination of the radical $R^{15}$ are carboxylic acids and their alkali metal salts (e.g. formic acid, acetic acid, 2-ethylhexanoic acid, sodium 2-ethyl-hexanoate), organic amines such as, for example, morpholine, triethylamine, pyrrolidine, dimethyltrimethylsilylamine, trimethylsilylmorpholine, n-butylamine, dimedone, sodium diethylmalonate, tributyltin hydride, N,N-dimethylbarbituric acid or ammonium formate. 2-Ethylhexanoic acid and sodium 2-ethyl-hexanoate are preferred.

The auxiliary is generally employed in a quantity of from 1 mol to 20 mol, preferably from 1.1 mol to 2 mol, based on 1 mol of the compounds of the general formula (V).

Examples of Pd catalysts which are suitable in the context of the process according to the invention are tetrakistriphenylphosphinepalladium (O) $(Pd(PPh_3)_4/PPh_3$, palladium dibenzylideneacetone $(Pd_2(dba)_3)$, $Pd_2(dba)_3 \times CHCl_3$, $Pd(dba)_2$, $PdCl_2$, $Pd(OAc)_2$, $PdCl_2(PhCN)_2$, $PdCl_2(CH_3CN)_2$ or $PdCl_2(PPh_3)_2$. Palladium dibenzylideneacetone and tetrakistriphenylphosphinepalladium are preferred.

The catalyst is generally employed in a quantity of from 0.0001 mol to 0.2 mol, preferably from 0.001 mol to 0.05 mol, based on 1 mol of the compounds of the general formula (V).

The elimination of the radical $R^{15}$ is generally carried out in a temperature range from 0° C. to 60° C., preferably from 20° C. to 30° C.

The elimination is generally carried out at atmospheric pressure. However, it is also possible to work at subatmospheric pressure or superatmospheric pressure (e.g. from 0.5 to 5 bar).

Amino-protecting groups in the context of the invention are the conventional amino-protecting groups used in peptide chemistry.

These include preferably: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl, allyloxycarbonyl, vinyloxycarbonyl, 2-nitrobenzyloxycarbonyl, 3,4,5-trimethoxybenzyloxycarbonyl, phthaloyl, 2,2,2-trichloroethoxycarbonyl, 2,2,2-trichloro-tert-butoxycarbonyl, menthyloxycarbonyl, 4-nitrophenoxycarbonyl, N-fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. Fmoc is particularly preferred.

The Hofmann rearrangement of the compounds of the general formula (VI) or (VIa) is in general carried out using alkali metal hypochlorites or alkaline earth metal hypochlorites in aqueous alkali metal hydroxide or alkaline earth metal hydroxide solution. Potassium hypochlorite in aqueous potassium hydroxide solution is preferred.

The Hofmann rearrangement is generally carried out in a temperature range from −15° C. to +50° C., preferably from −10° C. to +30° C. at atmospheric pressure.

The amino-protecting group is introduced by conventional methods in one of the above-listed solvents, preferably dioxane, in the presence of a base and in a temperature range from 0° C. to 60°C., preferably at room temperature and atmospheric pressure.

Suitable bases are the conventional basic compounds. These include preferably alkali metal hydroxides and alkaline earth metal hydroxides such as lithium hydroxide, sodium hydroxide, potassium hydroxide or barium hydroxide, alkali metal hydrogen carbonates and alkaline earth metal hydrogen carbonates such as lithium hydrogen carbonate, sodium hydrogen carbonate, potassium hydrogen carbonate or barium hydrogen carbonate, and alkali metal carbonates or alkaline earth metal carbonates such as sodium carbonate, potassium carbonate, or alkali metal alcoholates. Sodium hydrogen carbonate is particularly preferred.

The base is generally employed in a quantity of from 1 mol to 20 mol, preferably from 5 mol to 10 mol, based on 1 mol of the compounds of the general formula (VI).

The amino-protecting group is generally eliminated using the above-listed organic amines. Piperidine is preferred.

The base is generally employed in a quantity of from 1 mol to 100 mol, preferably from 20 mol to 60 mol, based on 1 mol of the protected compound.

The elimination is generally carried out in a temperature range from 0° C. to 60° C., preferably from 20° C. to 30° C. at atmospheric pressure.

The compounds of the general formula (II) are known per se or can be prepared according to published methods.

The alcohols of the general formula (III) are known.

The compounds of the general formulae (IV), (IVa) and (V) are novel and can be prepared, for example, as described above.

Some of the compounds of the general formulae (VI) and (VIa) are known, in which case they can be prepared as described above.

The process according to the invention is preferably used to prepare enantiomerically pure compounds of the general formula (I)

in which
A and L denote hydrogen,
D and E are identical or different and represent hydrogen, fluorine, chlorine, bromine, benzyl or hydroxyl or represent straight-chain or branched alkyl having up to 6 carbon atoms which is optionally substituted by halogen, benzyloxy or hydroxyl, by straight-chain or branched alkoxy, acyl or alkoxycarbonyl having in each case up to 4 carbon atoms or by a group of the formula —NR$^4$R$^5$,
in which
R$^4$ and R$^5$ are identical or different and denote hydrogen or straight-chain or branched alkyl having up to 4 carbon atoms,
or D and E together represent a radical of the formula

or =N—OH,
in which
R$^6$ and R$^7$ are identical or different and denote hydrogen, fluorine, chlorine, bromine, or straight-chain or branched alkyl having up to 6 carbon atoms, or denote benzyl or phenyl,
or
D and E together represent the radical of the formula =O or =S,
R$^2$ represents hydrogen or
represents Boc, benzyl, benzyloxycarbonyl, allyloxycarbonyl or 9-fluorenyl methyloxycarbonyl (Fmoc), or
represents straight-chain or branched alkyl having up to 6 carbon atoms which is optionally substituted by hydroxyl or formyl or by straight-chain or branched acyl having up to 4 carbon atoms or by phenyl or benzoyl, which are optionally substituted by halogen, nitro or cyano or by straight-chain or branched alkyl having up to 4 carbon atoms,
or
represents straight-chain or branched acyl having up to 6 carbon atoms,
or
represents benzoyl which is optionally substituted as described above,
or
represents a group of the formula —SO$_2$R$^8$,
in which
R$^8$ denotes straight-chain or branched alkyl having up to 6 carbon atoms, phenyl or benzyl, the latter radicals being optionally substituted up to 2 times by identical or different substituents consisting of halogen, hydroxyl, nitro, cyano, trifluoromethyl or trifluoromethoxy or of straight-chain or branched alkyl or alkoxy having in each case up to 4 carbon atoms or of the above-listed group of the formula —NR$^4$R$^5$,
in which
R$^4$ and R$^5$ have the meaning given above,
represents phenyl which is optionally substituted up to 2 times by identical or different substituents consisting of halogen, hydroxyl, nitro, trifluoromethyl, trifluoromethoxy, straight-chain or branched alkyl, acyl, alkoxy or alkoxycarbonyl having in each case up to 4 carbon atoms or of a group of the formula —NR$^6$R$^7$ or —SO$_2$R$^8$,
in which
R$^6$ and R$^7$ have the meaning given above,
or
represents an amino acid residue of the formula

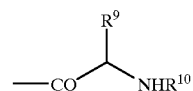

in which
R$^9$ denotes hydrogen, straight-chain or branched alkyl having up to 6 carbon atoms or benzyl,
and
R$^{10}$ denotes hydrogen, benzyloxy, Fmoc or tert-butoxycarbonyl,
R$^3$ represents hydrogen or represents straight-chain or branched alkyl having up to 6 carbon atoms or benzyl,
or
R$^2$ and R$^3$ together represent the radical of the formula =CHR$^{14}$,
in which
R$^{14}$ denotes hydrogen or straight-chain or branched alkyl having up to 6 carbon atoms which is optionally substituted by halogen or hydroxyl or by straight-chain or branched alkoxy or alkoxycarbonyl having in each case up to 4 carbon atoms,
T represents an oxygen or sulphur atom or represents the —NH group,
R$^1$ represents hydrogen or represents straight-chain or branched alkyl having up to 6 carbon atoms or phenyl, the latter radicals being optionally substituted up to 2 times by identical or different substituents consisting of hydroxyl, halogen, nitro, cyano, trifluoromethyl or trifluoromethoxy, of straight-chain or branched alkoxy, acyl or alkoxycarbonyl having in each case up to 4 carbon atoms, or of a group of the formula —NR$^4$R$^5$ or —SO$_2$R$^8$,
in which
R$^4$, R$^5$ and R$^8$ have the meaning given above,
or, if T represents the —NH group,
R$^1$ represents the group of the formula —SO$_2$R$^8$,
in which
R$^8$ has the meaning given above.
The process according to the invention is used with particular preference to prepare enantiomerically pure compounds of the general formula (I)
in which
A and L denote hydrogen,
or
D and E are identical or different and represent hydrogen, fluorine, chlorine, bromine, benzyl or hydroxyl or represent straight-chain or branched alkyl having up to 4 carbon atoms which is optionally substituted by hydroxyl or benzyloxy, or D and E together represent a radical of the formula

or =N—OH,
in which
R$^6$ and R$^7$ are identical or different and denote hydrogen, fluorine, chlorine, bromine or straight-chain or branched alkyl having up to 4 carbon atoms or denote phenyl, or
D and E together represent the radical of the formula =O or =S,
R$^2$ represents hydrogen, allyloxycarbonyl, benzyl, Boc or Fmoc, or
represents straight-chain or branched alkyl having up to 4 carbon atoms, or
represents straight-chain or branched acyl having up to 4 carbon atoms or represents a group of the formula —SO$_2$R$^8$,
in which
R$^8$ denotes straight-chain or branched alkyl having up to 4 carbon atoms, or denotes phenyl or benzyl, the latter radicals being optionally substituted by hydroxyl, fluorine, chlorine, bromine, nitro, cyano, methyl, ethyl or -methoxy,
or
represents an amino acid residue of the formula

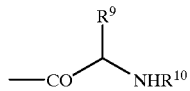

in which
R$^9$ denotes hydrogen, straight-chain or branched alkyl having up to 4 carbon atoms or benzyl,
and
R$^{10}$ denotes hydrogen, tert-butoxycarbonyl or Fmoc,
R$^3$ represents hydrogen or represents straight-chain or branched alkyl having up to 4 carbon atoms,
or
R$^2$ and R$^3$ together represent the radical of the formula =CHR$^{14}$,
in which
R$^{14}$ denotes hydrogen or straight-chain or branched alkyl having up to 4 carbon atoms,
T represents an oxygen or sulphur atom or the —NH group,
R$^1$ represents hydrogen or represents straight-chain or branched alkyl having up to 4 carbon atoms or phenyl, the latter radicals being optionally substituted by fluorine, chlorine, bromine, nitro, cyano, methoxy or ethoxy or by a group of the formula —NR$^4$R$^5$ or —SO$_2$R$^8$,
in which
R$^4$ and R$^5$ are identical or different and denote hydrogen, methyl or ethyl
and
R$^8$ has the meaning given above,
or, if T represents the —NH group,
R$^1$ represents the group of the formula —SO$_2$R$^8$, in which
R$^8$ has the meaning given above.

The process according to the invention is used with very particular preference to prepare enantiomerically pure compounds of the general formula (I)
in which
A, D, E and L represent hydrogen,
or
A and L represent hydrogen
and
D and E together form a double bond.

The process according to the invention enables access, in a highly enantioselective manner combined with quantitative yields, to enantiomerically pure cyclopentane- and -pentene β-amino acids of the general formula (I), which constitute valuable antimycotic and antibacterial medicaments.

EXAMPLE 1

4-Methylene-cyclopentane-1,2-dicarboxylic acid

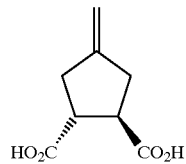

2.2245 kg (40 mol) of potassium hydroxide are dissolved in 15.7 l of water and the solution is cooled to room temperature. 2.2263 kg (10 mol) of diethyl 4-methylene-1,2-cyclopentane-dicarboxylate are dissolved in 15.7 l of ethanol, and the solution is run at room temperature into the potassium hydroxide solution. After stirring for 30 minutes at RT the ethanol is distilled off at 55° C. on a rotary evaporator. The aqueous solution which remains is washed with twice 5 l of diethyl ether, the ether phase is discarded, and the aqueous phase is cooled and adjusted to a pH of 2 using 3 l of concentrated hydrochloric acid. The mixture is then extracted 3 times with 9 l of ethyl acetate each time, and the ethyl acetate phase is dried over sodium sulphate and concentrated at 60° C. on a rotary evaporator.

Yield: 1.66 kg; 97.5% of theory; M.p.: 165–172° C.

EXAMPLE 2

4-Methylene-cyclopentane-1,2-dicarboxylic anhydride

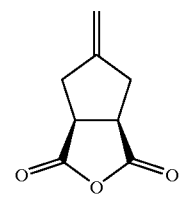

1325.6 g (7.79 mol) of 4-methylene-1,2-cyclopentane-dicarboxylic acid and 6 l of propionic anhydride are heated under reflux (160° C.) for 7 h. A portion of the propionic anhydride is distilled off at 80° C. on a rotary evaporator and the residue (2.165 kg) is distilled under a high vacuum.

Yield: 1014.9 g; 80.2% of theory; GC: 93.7% pure; B.pt.: 97–100° C. (0.5 mm Hg)

EXAMPLE 3

Cyclopentane-1,2-dicarboxylic anhydride

The preparation is carried out by analogy with that described for Example 2, starting from 29.9 g (189 mmol) of 1,2-cyclopentane-dicarboxylic acid.

Yield: 17.8 g (77%); B.pt.: 140° C. (0.1 mbar, bulb tube distillation)

EXAMPLE 4 AND EXAMPLE 5

Monoallyl (−)-1,2-cis-4-methylene-cyclopentane-1, 2-di-carboxylate, quinine salt × quinine Monoallyl (−)-1,2-cis-4-methylene-cyclopentane-1,2-dicarboxylate 750 g (4.93 mol) of 4-methylene-1,2-cyclopentane-dicarboxylic anhydride are dissolved in 34 l of diethyl ether and the solution is cooled to 0° C. 1.6 kg (4.9 mol) of (−)-quinine are added, the mixture is cooled to −10° C., 504.6 ml (7.4 mol) of allyl alcohol are added, and the mixture is stirred at from −10° C. to −5° C. for 4 h, with precipitation of Example 4. The product is filtered off with suction, washed with a total of 10 l of diethyl ether and dried in vacuo. 2217.7 g of the compound of Example 4 are suspended in 30 l of ethyl acetate and washed with 10 l of 1N hydrochloric acid. The combined hydrochloric acid phases are washed twice with ethyl acetate, and the combined ethyl acetate phases are washed with saturated sodium chloride solution, dried over sodium sulphate and concentrated at 50° C. on a rotary evaporator to give 859.2 g (83.5% of theory).

Enantiomeric excess: >99% (HPLC, Chiracel OD)
$^1$H-NMR (CDCl$_3$): δ=2.59–2.91 (4H), 3.11–3.28 (2H), 4.58 (2H), 4.94 (2H); 5.18–5.37 (2H); 5.80–5.97 (1H).

The aqueous hydrochloric acid phase is adjusted to a pH of 9.4 using 2.5 M sodium hydroxide solution, and the quinine which precipitates is filtered off with suction, washed with water and dried at 50° C. in a circulating-air drying cabinet.

Yield: M.p.: 160–162° C.

EXAMPLE 6

Monoallyl (−)-cis-cyclopentane-1,2-dicarboxylate

The preparation is carried out by analogy with that described for Example 4 and 5, starting from 13.8 g (98.6 imol) of the compound of Example 3.

Yield: 13.0 g (67%); $^1$H-NMR (CDCl$_3$): 1.56–2.20 (6H); 3.03–3.16 (2H); 4.08 (2H); 5.69–5.90 (2H); 5.82–6.00 (1H).

Enantiomeric excess e.e.: >98% (determined by HPLC after coupling of the carboxylic acid function with L-phenyl-glycinol)

The compounds listed in Table 1 are prepared in analogy to the procedure of Examples 4, 5 and 6:

TABLE 1

| Ex. No. | R$^{15}$ | Yield (% of th.) | e.e. (%) |
|---|---|---|---|
| 7 | —(CH$_2$)$_2$—CN* | 41 | 78 |
| 8 | —(CH$_2$)$_2$Si(CH$_3$)$_3$* | 87 | 64 |
| 9 | —CH(CH$_3$)$_2$* | 76 | 17 |
| 10 | —C$_2$H$_5$* | 74 | 88 |
| 11 | —CH$_3$* | 81 | 75 |
| 12 | —(CH$_2$)$_2$CH$_3$ | 72 | 98 |
| 13 | —(CH$_2$)$_3$CH$_3$ | 67 | 97.5 |
| 14 | —CH=CH—C$_6$H$_5$ | 82 | 94 |
| 15 | —CH$_2$—CH(CH$_3$)$_2$ | 69 | 95 |

* = in toluene at 0° C.

EXAMPLE 17

Allyl (−)-1,2-cis-2-aminocarbonyl-4-methylene-cyclopentane-1-carboxylate 1.145 kg (5.447 mol) of monoallyl (−)-1,2-cis- 4-methylene-1,2-cyclopentane-dicarboxylate are dissolved in 25 l of ethyl acetate, 729 ml (5.73 mol) of N-ethyl-morpholine are added, and 743.5 ml (5.73 mol) of isobutyl chloroformate are run in at −6° C. over the course of 20 minutes. The mixture is stirred at from −6° C. to −10° C. for 1 h and, at this temperature, 1276 ml (17.07 mol) of a precooled dilute aqueous ammonia solution are run in. The mixture is stirred at this temperature for 1 h, adjusted to a pH of 5 with dilute hydrochloric acid, the phases are separated, the aqueous phase is washed with 4 l of ethyl acetate, and the combined ethyl acetate phases are washed with twice 3 l of saturated sodium chloride solution, dried over sodium sulphate and concentrated on a rotary evaporator. The product crystallizes out by addition of 4 l of petroleum ether and is filtered off with suction, stirred with 4 l of petroleum ether, filtered off with suction, washed with 2 l of petroleum ether and dried in vacuo.

Yield: 996 g, 87.4% of theory; M.p.: 62° C.

EXAMPLE 18

Allyl (−) -cis-2-aminocarbonyl-cyclopentane-1-carboxylate

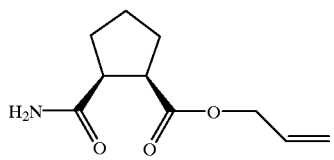

The preparation is carried out by analogy with that described for Example 17, starting from 12.7 g (64 mmol) of the compound of Example 6.

Yield: 9.9 g (78%); M.p.: 35° C.; $[\alpha]_D^{30}$=−10.4 (c=1.05, CHCl$_3$)

EXAMPLE 19

(−)-1,2-cis-2-Aminocarbonyl-4-methylene-cyclopentane-1-carboxylic acid, sodium salt

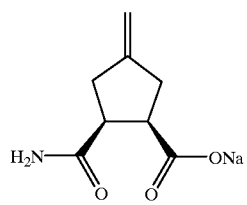

258 g (1.233 mol) of allyl (−)-1,2-cis-2-aminocarbonyl-4-methylene-1,2-cyclopentanecarboxylate are dissolved in 5 l of ethyl acetate under an argon atmosphere. A solution of 1.749 mol of 2-ethylhexanoic acid, sodium salt in 3.15 l ethyl acetate, 32.5 g (0.123 mol) of triphenylphosphine and 7.1 g (6.15 mmol) of tetrakis(triphenylphosphine)palladium are added, and the solution is stirred at RT for 2 h, with the product precipitating. The suspension is stirred to extract the product in 10 l of acetone, and the product is filtered off with suction and dried in vacuo.

Crude yield: 281.1 g; contaminated with ethylhexanoic acid, sodium salt; $^1$H-NMR (D$_2$O): δ=2.54–2.82 (4H); 3.08–3.25 (2H); 5.01 (2H)

EXAMPLE 20

(−)-1,2-cis-2-Aminocarbonyl-cyclopentane-1-carboxylic acid, sodium salt

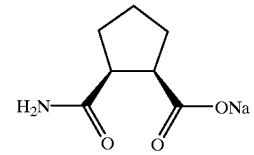

The preparation is carried out analogously with that described for Example 19, starting from 9.85 g (50.0 mmol) of the compound of Example 18.

Yield: 7.1 g (79%); $^1$H-NMR (CDCl$_3$): δ=1.52–2.14 (6H); 2.95–3.18 (2H).

EXAMPLE 21

(−) -1,2-cis-2-Aminocarbonyl-4-methylene-cyclopentane-1-carboxylic acid

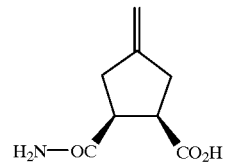

104.5 g (0.5 mol) of allyl (−)-1,2-cis-2-aminocarbonyl-4-methylene-1,2-cyclopentanecarboxylate are dissolved under a nitrogen atmosphere in 1 l of acetic acid and 119 ml (0.75 mol) of 2-ethylhexanoic acid. After addition of 13.1 g (0.05 mol) of triphenylphosphine and 3 g (0.005 mol) of bis (dibenzylideneacetone)palladium(0) the reaction solution is stirred at RT for 5 h, the product crystallizing out. The product is filtered off with suction, washed with 50 ml of ethyl acetate and dried in vacuo.

Yield: 63.4 g (75% of theory)

EXAMPLE 22

Aqueous solution of (−)-1,2-cis-2-amino-4-methylene-cyclopentanecarboxylic acid

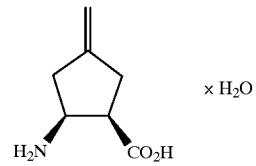

817 g (4.27 mol) of (−)-1,2-cis-2-aminocarbonyl-4-methylene-1,2-cyclopentanecarboxylic acid, sodium salt, are added at 0° C. to a solution of 478.45 g (8.54 mol) of potassium hydroxide in 9 l of water. 3.12 l of a 2.5 molar potassium hypochlorite solution are added, and the mixture is stirred overnight at this temperature. The solution is adjusted to a pH of 2 with 5N hydrochloric acid, washed 4 times with diethyl ether, and the aqueous phase is adjusted to a pH of 6.9 with 5N sodium hydroxide solution and filtered off with suction over kieselguhr.

EXAMPLE 23

Aqueous solution of (−)-1,2-cis-2-amino-cyclopentane-1-carboxylic acid

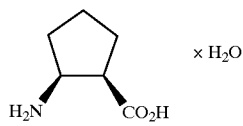

The preparation is carried out analogously to that described for Example 22, starting from 7.0 g (39.0 mmol) of the compound of Example 20.

EXAMPLE 24

(−) -1,2-cis-2-N-(9-Fluorenylmethoxycarbonyl)-amino-4-methylene-1-cyclopentane-carboxylic acid

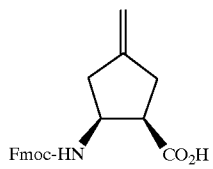

2.21 kg (26.34 mol) of sodium hydrogen carbonate are added to 21.18 l (about 3.7 mol) of the aqueous solution of (−)-1,2-cis-2-amino-4-methylene-cyclopentanecarboxylic acid, and the mixture is stirred at RT for 15 minutes. A solution of 1.02 kg (3.01 mo) of N-(9-fluorenylmethoxycarbonyloxy)-succinimide in 5.4 l of dioxane is run in, and the mixture is stirred at RT for 5 h. The solution is filtered and washed with 20 l of diethyl ether, the organic phase is washed with dilute sodium carbonate solution and the aqueous basic product phases are adjusted to a pH of 2 at RT using dilute hydrochloric acid. The mixture is washed several times with diethyl ether, and the combined organic phases are dried over sodium sulphate and concentrated on a rotary evaporator to give an oil.

Yield: 1.47 kg; 104.6% of theory; $[\alpha]_D^{20}$=−18.8 (c=1, MeOH); M.p.: 137° C.

Enantiomeric excess e.e.: >99% (HPLC, Chiralpak AS)

EXAMPLE 25

(−)-1,2-cis-2-(tert-Butyloxycarbonyl)amino-cyclopentane-1-carboxylic acid

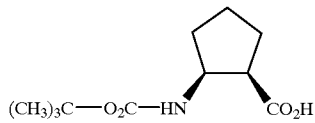

To the neutralized aqueous solution of the compound of Example 23 are added 15 g of sodium carbonate (pH=9.8) and 200 ml of dioxane. 9.2 g (42 mmol) of di-tert-butyl dicarbonate are added at 0° C., and the mixture is stirred at 0° C. for 10 min and at room temperature for 20 h. The reaction mixture is adjusted to a pH of 2 with dilute hydrochloric acid and is extracted with three times 200 ml of ethyl acetate. The combined organic phases are washed with saturated NaCl solution, dried over $Na_2SO_4$ and concentrated on a rotary evaporator. The residue is chromatographed over silica gel with dichloromethane/methanol (20:1) as eluent (Rf=0.35).

Yield: 7.34 g (82%); $[\alpha]_D^{20}$=−35.0 (c=1.2, $CHCl_3$)

EXAMPLE 26

(−)-1,2-cis-2-Amino-4-methylene-cyclopentane carboxylic acid

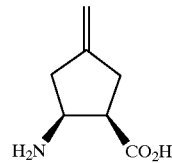

A suspension of 1.47 kg (3.76 mol) of (−)-1,2-cis-2-N-(9-fluorenylmethoxycarbonyl)-amino-4-methylene-1-cyclopentane carboxylic acid in 13 l of piperidine is stirred at room temperature for 3 h until a clear solution is formed, after which 8 l of piperidine are distilled off under a steam jet vacuum (60° C. bath temperature), 10 l of diethyl ether are added, and the mixture is stirred overnight in a rotary evaporator. The suspension is transferred to a full-aperture drum, 10 l of diethyl ether are added, the mixture is stirred for 2 h and the product is filtered off with suction. On the suction filter, the solid is stirred three times with 3 l of diethyl ether each time and sucked dry, and is dried over phosphorus pentoxide under a high vacuum at room temperature for 3 h to give 377 g of the free amino acid. The product is dissolved in 6.6 l of ethanol/water (9:1) to give a clear solution and left to crystallize out overnight. The product is filtered off, washed with 0.2 l of 95% ethanol and dried over phosphorus pentoxide in vacuo.

Yield: 214.5 g;

The filtrate is concentrated on a rotary evaporator and crystallized as described above from ethanol/water (9:1).

Total yield: 333.2 g; 63% of theory; M.p.: 222° C.; $[\alpha]_D^{20}$=−31.6 (c=1, $H_2O$)

EXAMPLE 27

(−)-1,2-cis-2-Amino-4-methylene-cyclopentane-carboxylic acid hydrochloride

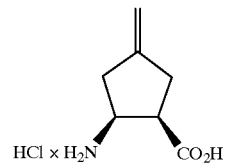

341.7 g (2.42 mol) of (−)-1,2-cis-2-amino-4-methylene-cyclopentane-carboxylic acid are dissolved in 8 l of double-distilled water, the solution is filtered with suction through a sintered glass suction filter, and the suction filter is washed with 0.2 l of double-distilled water. 2.42 ml of 1 N hydrochloric acid are added to the solution in a rotary evaporator flask, and the solution is concentrated to remove the residual solvents until crystallization commences (bath 65° C.), when twice 2 l of double-distilled water are added; the mixture is concentrated to dryness and the residue is dried subsequently at 40° C. for 30 minutes. It is then dried over phosphorus pentoxide under a high vacuum for 84 h and over potassium hydroxide for 24 h.

Yield: 421.1 g; 97.7% of theory; $[\alpha]_D^{20}$=−11.6 (c=1, $H_2O$)

EXAMPLE 28

(−)-1,2-cis-2-Amino-cyclopentane-1-carboxylic acid hydrochloride

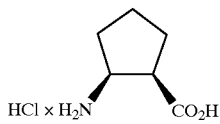

A solution of the compound of Example 25 (3.90 g, 17.0 mmol) in 30 ml of 4 N HCl in dioxane is stirred at room temperature for 2 h. The precipitated product is filtered off with suction, washed with dioxane and ether and dried under a high vacuum for 15 h.

Yield: 2.39 g (84%); $[\alpha]_D^{20}$=−5.7 (c=0.99, $H_2O$)

Enantiomeric excess e.e.: >95% (Hplc, Chiralpak AS after conversion to the N-Fmoc-protected compound)

We claim:

1. Enantiomerically pure compounds of the general formula (IV)

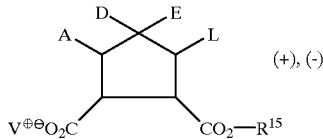

in which

A and L denote hydrogen or

A and D or E and L in each case together form a double bond,

D and E are identical or different and represent hydrogen, halogen or hydroxyl or represent straight-chained or branched-chained alkyl having up to 8 carbon atoms which is optionally mono- to disubstituted by identical or different substituents consisting of halogen, hydroxyl, phenyl, benzyloxy or carboxyl or of straight-chain or branched alkoxy, acyl or alkoxycarbonyl having in each case up to 6 carbon atoms or of a group of the formula —$NR^4R^5$, in which $R^4$ and $R^5$ are identical or different and denote hydrogen, phenyl or straight-chain or branched alkyl having up to 6 carbon atoms, or D and E together represent a radical of the formula

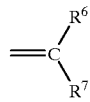

or =N—OH, in which $R^6$ and $R^7$ are identical or different and denote hydrogen or halogen or straight-chain or branched alkyl, alkoxy or oxyacyl having in each case up to 8 carbon atoms, or denote benzyl or phenyl, or D and E together represent the radical of the formula =O or =S, $R^{15}$ represents straight-chain or branched alkyl or represents alkenyl having in each case up to 5 carbon atoms, which are optionally substituted by cyano, trimethylsilyl, phenyl or trichloromethyl, and V represents a chiral amine base.

2. Enantiomerically pure compounds according to claim 1, wherein the chiral amine base is an alkaloid or cinchona alkaloid.

3. Enantiomerically pure compounds according to claim 2, wherein the chiral amine base is quinine, hydroquinine, cinchonidine, epiquinidine, epicinchonidine, cinchonine, epicinchonine, epiquinine, hydroquinidine, 4-chlorobenzoate-epiquinine or 4-chlorobenzoate-epicinchonine.

4. Enantiomerically pure compounds of the general formula (V)

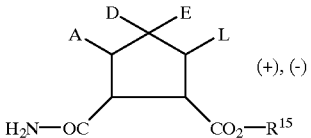

in which

A and L denote hydrogen or

A and D or E and L in each together form a double bond,

D and E are identical or different and represent hydrogen, halogen or hydroxyl or represent straight-chain or branched alkyl having up to 8 carbon atoms which is optionally mono- to disubstituted by identical or different substituents consisting of halogen, hydroxyl, phenyl, benzyloxy or carboxyl or of straight-chain or branched alkoxy, acyl or alkoxycarbonyl having in each case up to 6 carbon atoms or of a group of the formula —$NR^4R^5$, in which $R^4$ and $R^5$ are identical or different and denote hydrogen, phenyl or straight-chain or branched alkyl having up to 6 carbon atoms, or D and E together represent a radical of the formula

or =N—OH, in which $R^6$ and $R^7$ are identical or different and denote hydrogen or halogen or straight-chain or branched alkyl alkoxy or oxyacyl having in each case up to 8 carbon atoms, or denote benzyl or phenyl, or D and E together represent the radical of the $R^{15}$ represents straight-chain or branched alkyl or represents alkenyl having in each case up to 5 carbon atoms, which are optionally substituted by cyano, trimethylsilyl, phenyl or trichloromethyl.

5. Process for the preparation of enantiomerically pure cyclopentane- and -pentene β-amino acids of the general formula (I)

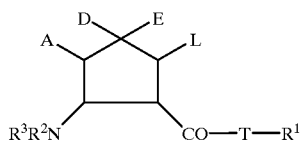
(I)

in which

A and L denote hydrogen or

A and D or E and L in each case together form a double bond,

D and E are identical or different and represent hydrogen, halogen or hydroxyl or represent straight-chain or branched alkyl having up to 8 carbon atoms which is optionally mono- to disubstituted by identical or different substituents consisting of halogen, hydroxyl, phenyl, benzyloxy or carboxyl or of straight-chain or branched alkoxy, acyl or alkoxycarbonyl having in each case up to 6 carbon atoms or of a group of the formula —NR$^4$R$^5$, in which R$^4$ and R$^5$ are identical or different and denote hydrogen, phenyl or straight-chain or branched alkyl having up to 6 carbon atoms, or D and E together represent a radical of the formula

or =N—OH, in which

R$^6$ and R$^7$ are identical or different and denote hydrogen or halogen or straight-chain or branched alkyl, alkoxy or oxyacyl having in each case up to 8 carbon atoms, or denote benzyl or phenyl, or D and E together represent the radical of the formula =O or =S, R$^2$ represents hydrogen;

R$^3$ represents hydrogen;

T represents an oxygen;

R$^1$ represents hydrogen;

which comprises converting meso-dicarboxylic acid anhydrides of the general formula (II)

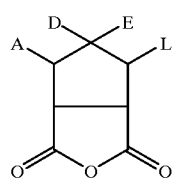
(II)

in which

A, D, E and L have the meaning given above by an asymmetric alcoholysis with alcohols of the general formula (III)

R$^{15}$—OH  (III)

in which

R$^{15}$ represents straight-chain or branched alkyl or represents alkenyl having in each case up to 5 carbon atoms, which are optionally substituted by cyano, trimethylsilyl, phenyl or trichloromethyl, and in the presence of equimolar amounts of a chiral amine base which is present in enantiomerically pure form, in inert solvents and initially via the intermediate, enantiomerically pure salt stage of the general formula (IV)

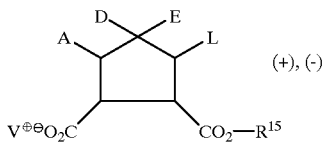
(IV)

in which

A, D, E, L and R$^{15}$ have the meaning given above and

V represents the chiral amine base, to the enantiomerically pure compounds of the general formula (IVa)

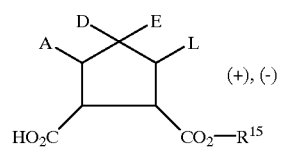
(IVa)

in which

A, D, E, L and R$^{15}$ have the meaning given above, subsequently, following activation of the free carboxylic acid function by reaction with liquid NH$_3$, the enantiomerically pure amides of the general formula (V)

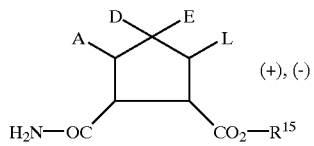
(V)

in which

A, D, E, L and R$^{15}$ have the meaning given above, are prepared, in a further step the products are converted, by elimination of the radical R$^{15}$ in inert solvents, enzymatically or in the presence of a Pd catalyst, and in each case depending on a nucleophilic auxiliary, into the compounds of the general formula (VI) or (VIa)

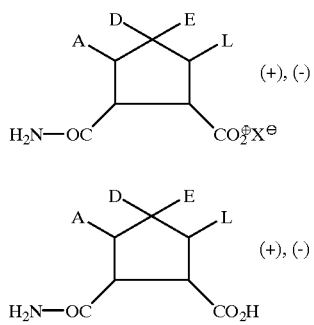

in which

A, D, E and L have the meaning given above, and

X represents an alkali metal or alkaline earth metal atom, and finally a Hofmann rearrangement is carried out using alkali metal hypochlorites or alkaline earth metal hypochlorites in aqueous alkali metal hydroxide or alkaline earth metal hydroxide solution, the free amine function is initially blocked in solution with a typical amino-protecting group, which is eliminated by conventional methods after isolation of the protected compounds in accordance with conventional conditions to obtain the respective pure enantiomer.

* * * * *